United States Patent [19]

Hawiger et al.

[11] Patent Number: 4,661,471
[45] Date of Patent: Apr. 28, 1987

[54] METHOD OF INHIBITING AND INDUCING HUMAN PLATELET AGGREGATION

[75] Inventors: Jack J. Hawiger, Chestnut Hill; Sheila Timmons, Boston, both of Mass.; Thomas J. Lukas, Nashville, Tenn.; Marek Kloczewiak, Boston, Mass.

[73] Assignee: New England Deaconess Hospital, Boston, Mass.

[21] Appl. No.: 599,477

[22] Filed: Apr. 10, 1984

[51] Int. Cl.⁴ .................... C07K 7/08; A61K 37/02
[52] U.S. Cl. ........................................ 514/13; 514/16; 530/326
[58] Field of Search ............... 260/112.5 R; 435/214; 424/22; 514/13, 16; 530/326

[56] References Cited

U.S. PATENT DOCUMENTS

| | | | |
|---|---|---|---|
| 4,303,592 | 12/1981 | Laura et al. | 435/214 |
| 4,351,337 | 9/1982 | Sidman | 424/22 |
| 4,455,290 | 6/1984 | Olepa et al. | 260/112.5 R |
| 4,476,116 | 10/1984 | Anik | 260/112.5 R |

OTHER PUBLICATIONS

"Localization of a Fibrin α-Chain Polymerization Site within Segment Thr-374 to Glu-396 of Human Fibrinogen" Proc. Natl. Ac. Sci., (USA), 81, pp. 5980-5984 (1984).
Biochemistry, 1982, vol. 21, No. 6, pp. 1414-1420-Isolation, Characterization and Synthesis of Peptides from Human Fibrinogen that Block the Staphylococcal Clumping Reaction and Construction of a Synthetic Particle.
Biochemical and Biophysical Research Communications, vol. 107, No. 1, Jul. 16, 1982, pp. 181-187-Localization of a Site Interacting with Human Platelet Receptor on Carboxy-Terminal Segment of Human Fibrinogen Chain.
Thrombosis Research 29; 249-255, 1983—Fibrinogen Site for Platelets.

Primary Examiner—Delbert R. Phillips
Attorney, Agent, or Firm—Lahive & Cockfield

[57] ABSTRACT

A method of inhibiting thrombin or ADP-induced human platelet aggregation by fibrinogen has been developed. The administration of the small molecular weight peptide or the synthetic inhibitory molecule of the invention significantly inhibits thrombin or ADP-modified human platelets binding of fibrinogen, a plasma protein necessary for platelet aggregation. The method of the invention is useful for inhibiting of the formation of hemostatic platelet plugs and of the initiation of thrombotic lesions. The blockage caused by hemostatic platelet plugs and the damage caused by thrombotic lesions are major factors in heart disease and stroke. The invention also includes a method of inducing the formation of thrombin or ADP-modified platelet aggregates by administration of a synthetic aggregating molecule which represents a functional substitute for fibrinogen.

17 Claims, 1 Drawing Figure

METHOD OF INHIBITING AND INDUCING HUMAN PLATELET AGGREGATION

The invention described herein was made, in part, in the course of work under research grants numbers HL-30649, HL-3,0648, and GM-30861, from the National Institutes of Health, U.S. Public Health Service.

BACKGROUND OF THE INVENTION

The present invention relates to aggregation of human platelets. More particularly, the invention relates to a method of inhibiting thrombin or ADP-induced fibrinogen aggregation of human platelets as well as the construction of a synthetic platelet aggregation inducing molecule.

A number of different mechanisms have been disclosed which lead to the aggregation of human platelets to initiate blood clots (thrombi). One such mechanism is the thrombin or ADP-induced platelet aggregation cross-linked by the multivalent molecule, fibrinogen. Thrombin and ADP induce modification of the platelet structure, allowing interaction between platelets and fibrinogen to form aggregates. While the exact mechanism is not clear, one theory for this interaction is that thrombin and ADP cause a stereochemical change of the glycoprotein structure of the platelet cell membrane. The stereochemical change appears to create the specific receptor site on the platelet so that platelet binding regions on the fibrinogen molecule can react with this receptor site to form the aggregate. Until recently, the location of the platelet binding regions of human fibrinogen were unknown. In 1982, Hawiger, Timmons, Kloczewiak, Strong and Doolittle demonstrated that the primary fibrinogen interaction site with human platelets is located on the gamma chain of fibrinogen. See Proc. Natl. Acad. Sci. USA 79:2068-2071 (1982). In a later paper, Kloczewiak, Timmons and Hawiger demonstrated that the platelet binding region on fibrinogen was contained within the carboxyl terminal 27 peptide residues of the gamma chain and that a 15 peptide carboxyl terminal fragment of this molecule could block fibrinogen platelet aggregation. See Biochem. and Biophy. Rsc. Comm. 107:181-187 (1982).

Fibrinogen is important in the formation of hemostatic platelet plugs and initiation of thrombotic lesions. Blockage caused by these plugs and the damage caused by thrombotic lesions are major factors in heart disease and stroke. Much research has been directed toward developing drugs which will dissolve already formed blood clots but most of these drugs have not been particularly effective. Recently, reports on the use of tissue plasminogen activator, a molecule which modifies circulating plasminogen molecules to form plasmin, an enzyme that dissolves blood clots, have been given much publicity. While enzymatic methods of dissolving clots may help minimize the after effects of heart attacks, a pharmaceutical preparation which will inhibit platelet aggregation prior to occlusion of the blood vessels may prevent the initial blockage responsible for cardiac or cerebral infarction.

Alternatively, platelet aggregation promoting molecules may have a variety of uses. For example, a number of patients, e.g., some bleeders, may be lacking fibrinogen due to a genetic deficiency or due to excessive consumption in circulation. A synthetic platelet aggregating molecule can promote platelet plug formation to arrest bleeding and help these patients to lead normal lives.

Accordingly, an object of the invention is to develop a method of inhibiting thrombin or ADP-induced fibrinogen aggregation of human platelets. Another object of the invention is to provide a molecule which promotes thrombin or ADP-induced platelet aggregation. A further object of the invention is to provide a synthetic molecule which inhibits thrombin or ADP-induced fibrinogen platelet aggregation with significant circulation time in the blood stream. These and other objects and features of the invention will be apparent from the summary, the drawing and the description.

SUMMARY OF THE INVENTION

The present invention features a method of inhibiting thrombin or ADP-induced fibrinogen aggregation of human platelets. The invention also features a series of synthetic molecules which promote or inhibit thrombin or ADP-induced human platelet aggregation.

In particular, the method of invention includes the step of incubating human platelets with a peptide having a carboxyl terminal sequence Lys-X-X-X-Asp-X-COOH where each X is individually selected from a group consisting of amino acids. Preferably, the carboxyl terminal sequence is Lys-Gln-Ala-Gly-Asp-Val-COOH.

Incubation of the platelets with thrombin or ADP may be prior to or simultaneous with the peptide incubation. In one embodiment, thrombin or ADP-induced fibrinogen aggregation of human platelets is inhibited by the incubation of the platelets with a peptide having 6-14 residues containing this carboxyl terminal sequence. Preferably, the peptide is a dodecapeptide having the sequence H$_2$N-His-His-X-X-X-X-Lys-X-X-X-Asp-X-COOH where each X is individually selected from a group consisting of amino acids. Most preferably, the dodecapeptide has the sequence H$_2$N-His-His-Leu-Gly-Gly-Ala-Lys-Gln-Ala-Gly-Asp-Val-COOH.

The invention further features a method for inhibiting thrombin or ADP-induced fibrinogen aggregation of human platelets by incubating human platelets with a synthetic molecule having the carboxyl terminal sequence Cys-X-X-X-X-His-His-X-X-X-X-Lys-X-X-X-Asp-X-COOH where each X is individually selected from a group consisting of amino acids. Preferably, the synthetic molecules have the carboxyl terminal sequence Cys-Tyr-Gly-Gln-Gln-His-His-Leu-Gly-Gly-Ala-Lys-Gln-Ala-Gly-Asp-Val-COOH.

In one embodiment, human platelets are incubated with a cystinyl-linked dimer of this heptadecapeptide while in another embodiment, the synthetic molecule consists of this heptadecapeptide grafted to a polymeric backbone, e.g., a protein, most preferably human serum albumin, at a ratio such that each polymer molecule contains not more than one heptadecapeptide. This synthetic peptide-polymer has a longer inhibitory effect because it is not as easily cleared from the blood stream.

The invention also features a method of inducing thrombin or ADP-induced aggregation of human platelets in the absence of fibrinogen by incubating the platelets with a synthetic aggregation molecule. This method includes the step of incubating the platelets with a molecule formed of a plurality of peptides having the carboxyl terminal sequence

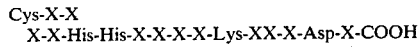
Cys-X-X-X-X-His-His-X-X-X-X-Lys-XX-X-Asp-X-COOH grafted to a polymeric backbone. Each X is individually selected from a group consisting of amino acids. Preferably, the synthetic molecule has the carboxyl terminal sequence

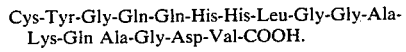
Cys-Tyr-Gly-Gln-Gln-His-His-Leu-Gly-Gly-Ala-Lys-Gln Ala-Gly-Asp-Val-COOH.

The preferred polymeric backbone is a protein, most preferably human serum albumin. Any amino acids may be used in the invention but naturally occurring amino acids are preferable.

BRIEF DESCRIPTION OF THE DRAWING

The sole figure of the drawing illustrates the inhibition of ADP-induced fibrinogen dependent platelet aggregation caused by incubation with various peptides of the invention.

DESCRIPTION

Figure 1:
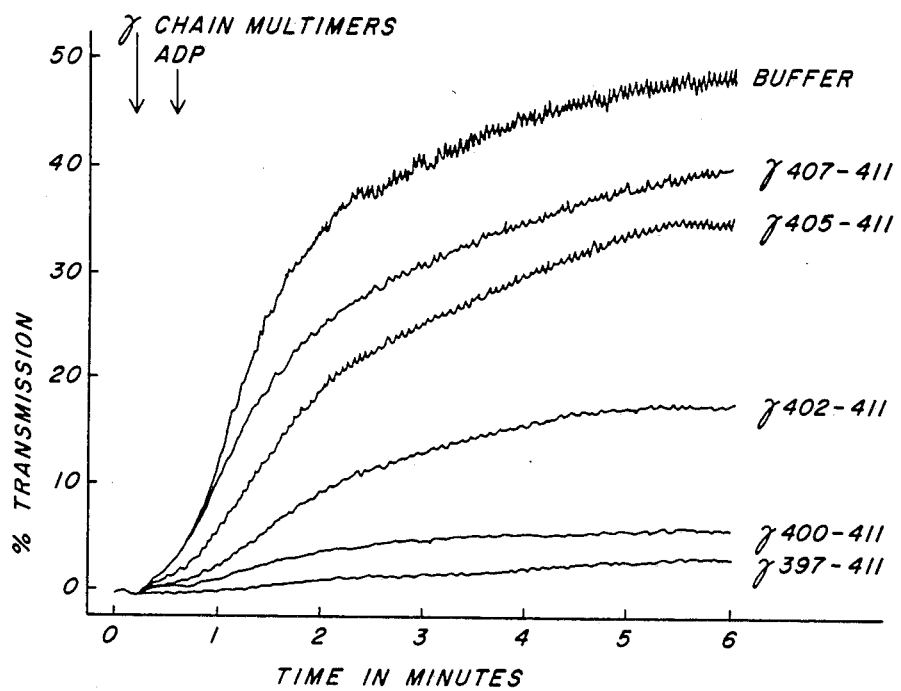

The present invention is based, in part, on the discovery that the primary attachment site on the fibrinogen molecule in the thrombin or ADP-induced fibrinogen aggregation of human platelets is located in the 12 carboxyl terminal residues of the gamma chain. These discoveries provide the basis for a method of inhibiting thrombin or ADP-induced fibrinogen aggregation of human platelets as well as providing the basis for the fabrication of molecules which can promote or inhibit this reaction.

The synthetic peptides described herein were synthesized in a manual shaker apparatus (Chipco Manufacturing) following the solid phase procedure of Barany and Merrifield described in *The Peptides Analysis, Synthesis, and Biology* (Gross and Meinhoper, Eds.), Vol. 2, pp. 1-284 (Academic Press, 1980). An aminomethyl resin (0.45 M/g) was derivatized with tertbutoxycarbonyl ("Boc")-Val-(4-oxymethyl) phenylacetic acid. The general solid phase synthesis protocol uses the following chemicals: 50% trifluoracetic acid ("TFA") for deprotection, 5% triethylamine for neutralization and a 2-3 fold excess of preformed Boc-amino acid symmetric anhydrides for couplings except for glutamine and histidine residues where direct dicylcohexylcarbodiimide coupling was used. The level of resin substitution, completeness of coupling, and deprotections were measured by quantitative ninhydrin reactions. The protecting groups and the peptide-resin link were cleaved by reaction in liquid HF/anisole (9:1 v/v) for one hour at 0° C. After evaporation of the HF, the resin was washed twice with ninhydrin ethylether, and crude peptides were extracted with 10% acetic acid and freeze-dried.

These lyophilized peptides were dissolved in 10% acetic acid, the insoluble material was removed by filtration, and the peptides were purified by high pressure liquid chromatography (HPLC) using a Beckman 430 chromatograph and Whatman preparative column. The absorbed peptide was eluted from the column with 0.1% (w/v) TFA until absorbancy at 214 nm returned to the base line, then a linear gradient of acetonitrile, from 0 to 80% concentration with 0.1% TFA, was applied for 100 minutes. The main peptide peak was collected and freeze dried.

Cysteine-containing peptides were converted to cystine cross-linked peptides by oxidation with the potassium ferricyanide. The cysteine-containing peptide was dissolved in 0.2 M Tris-HCl buffer, pH 7.4, at approximately 10mg/ml and was mixed with a 2 M excess of potassium ferricyanide and incubated at room temperature for 2 hours. After acidification, the peptide was mixed with AGI×8 (Bio Rad) resin to remove inorganic reagents and the supernatent was rechromatographed on an analytical column. The resulting main peptide peak was collected and freeze-dried.

The synthetic aggregation molecule was formed by dissolving 10 mg/ml human serum albumin (Miles Laboratories) in 0.1 M $Na_2HPO_4$ and mixing the albumin with a 10-fold molar excess of 17.9 mM N-succinimidyl (p-azidophenyldithio) propionate (Pierce) in dioxane to introduce additional sulfhydryl residues in the albumin. The reaction was carried out at 4° C. in the dark for one hour before the mixture was dialyzed, in the dark, against several changes of distilled water containing 1 mM mercaptoethanol and then against water. A 10-fold molar excess of the heptadecapeptide containing the cysteinyl terminal residue was added to the modified albumin in 0.05 M Tris-HCL buffer and free sulfhydryl residues were oxidized with potassium feracynanide. After oxidation, the whole mixture was acidified to pH 3 with acetic acid and mixed for a few minutes with AGI×8 resin. The resin was centrifuged and the supernatent dialyzed against 0.15 M sodium chloride. To form the albumin linked inhibitory molecule, the 10-fold excess of the cysteinyl peptide was replaced by 1:1 molar ratio of the cysteinyl peptide to albumin.

The following nonlimiting experiments illustrate the efficiency of the invention. All of these experiments use the reagents formed by the procedures delineated above.

EXPERIMENT 1

The following experiment illustrates that the peptides of the invention can inhibit fibrinogen binding to platelets. Human platelets at a concentration of $10^8$ cells/0.5 ml were treated with 5-10 micromoles of ADP. Various concentrations of the inhibitory peptides were mixed with the platelets and then 0.17 M $^{125}$I-labelled fibrinogen was added to the solution. The $IC_{50}$ or 50% inhibition of fibrinogen binding was determined for each peptide by allowing the reaction to proceed to a conclusion, separating the platelets from unbound $^{125}$I-fibrinogen and determining the amount of labelled fibrinogen bound to the platelets. The less labelled fibrinogen bound to the platelets, the better the inhibition. The heptadecapeptide and the dodecapeptide both had $IC_{50}$ values of 28 M, and the decapeptide and heptapeptide each had a $IC_{50}$ of about 97 M, illustrates that below 12 residues, part of the inhibition reaction is lost. Both acetylation of the dodecapeptide with acetic anhydride, which modifies the lysine residue, and trypsin cleavage of the dodecapeptide, which cleaves the bond between the lysine and glycine residues, abolish the inhibitory activity thereby illustrating that at least six residues, including the lysine, are needed for the inhibition reaction.

EXPERIMENT 2

The effectiveness of the invention at inhibiting fibrinogen cross-linked aggregation of platelets was demonstrated by the following experiment. A 60 M concentration of a variety of synthetic peptides of the invention was added to $10^8$ platelets which had been treated with 5-10 micromoles of ADP. At time zero, 7 micromoles of gamma chain fibrinogen multimers was added and the transmission of the solution was monitored for platelet aggregate formation. FIG. 1 illustrates the results of this experiment. As is evident from the Figure, the dodecapeptide caused almost complete inhibition of the aggregation reaction (transmission stayed near zero) while the shorter peptides caused some inhibition but not as complete as that of the dodecapeptide. The control buffer solution, a solution which does not contain any peptide, had substantial aggregation. While gamma chain multimers were used, similar results have been obtained with bivalent fibrinogen molecules.

EXPERIMENT 3

In this experiment, a synthetic clumping molecule formed of a human serum albumin backbone having a plurality of sulfhydral-linked cysteinyl heptadecapeptides attached thereto was tested to determine whether it would cause aggregation of platelets. Ten micromoles of ADP was added to $10^8$ platelets which had been separated from the plasma proteins. The addition of 2.5 micromoles of the synthetic peptide-albumin conjugate cause significant aggregation. If the dodecapeptide is added to the platelets prior to the addition of the synthetic peptide-albumin conjugate, the aggregation reaction is inhibited thereby illustrating that the same aggregation mechanism as in fibrinogen is used. As a negative control, human serum albumin, prepared the same way as the conjugate except but lacking the heptadecapeptide side groups, was found not to aggregate the platelets thereby establishing that the peptide-albumin conjugate causes a true aggregation reaction.

One potential problem which might develop with the use of small peptides as a method of preventing platelets aggregation is that small peptides are cleared from the bloodstream in a very short time. By conjugating the synthetic peptides to human serum albumin at a concentration of no more than one peptide per albumin molecule, a larger, hopefully more stable, platelet aggregation inhibitory molecule can be formed. These synthetic molecules may help eliminate some of the biohazards associated with transfusions, e.g. hepatitis, CMV virus and AIDS, by limiting the need for whole blood transfusions.

The foregoing description is purely illustrative and other skilled in the art may determine other modifications or variations of the method and products of the invention. Such other modifications or variations are included within the following claims.

What is claimed is:

1. A method for inhibiting thrombin or ADP-induced fibrinogen aggregation of human platelets comprising the step of incubating human platelets with a synthetic peptide analog of the platelet receptor recognition site of fibrinogen which contains 6-14 residues having a carboxyl terminal sequence Lys-X-X-X-Asp-Val-COOH where each X is individually selected from a group consisting of amino acids.

2. The method of claim 1 wherein said synthetic peptide analog has the carboxyl terminal sequence Lys-Gln-Ala-Gly-Asp-Val-COOH.

3. The method of claim 1 wherein said synthetic peptide analog is a dodecapeptide having the sequence H$_2$N-His-His-X-X-X-X-Lys-X-X-X-Asp-Val-COOH where each X is individually selected from a group consisting of amino acids.

4. The method of claim 3 wherein said synthetic peptide analog has the carboxyl terminal sequence H$_2$N-His-His
Leu-Gly-Gly-Ala-Lys-Gln-Ala-Gly-Asp-Val-COOH.

5. A method of inhibiting thrombin or ADP-induced fibrinogen aggregation of human platelets comprising the step of incubating human platelets with a molecule having a carboxyl terminal sequence consisting of Cys-X-X-X-X-His-His-X-X-X-X-Lys-X-X-X-Asp-Val-COOH where each X is individually selected from a group consisting of amino acids, where said carboxyl terminal sequence is a synthetic peptide analog of the platelet receptor recognition site of fibrinogen.

6. The method of claim 5 wherein said molecule has the carboxyl terminal sequence Cys-Tyr-Gly-Gln-Gln-His-His-Leu-Gly-Gly-Ala-Lys-Gln-AlaGly-Asp-Val-COOH.

7. The method of claim 5 wherein said molecule comprises a cystinyl-linked dimer of said carboxyl terminal sequence.

8. The method of claim 6 wherein said molecule comprises a cystinyl-linked dimer of said carboxyl terminal sequence.

9. The method of claim 5 wherein said molecule comprises said carboxyl terminal sequence grafted to a carrier molecule backbone in a proportion such that each carrier molecule backbone contains no more than one of said synthetic peptide analogs having this carboxyl terminal sequence.

10. The method of claim 9 wherein said carrier molecule backbone comprises a protein.

11. The method of claim 9 wherein said carrier molecule backbone comprises human serum albumin.

12. A method of aggregating thrombin or ADP-modified human platelets in the absence of fibrinogen comprising the step of forming an artificial aggregation molecule by grafting to a carrier molecule backbone a plurality of synthetic peptide analogs of the platelet receptor recognition site of fibrinogen each having the carboxyl terminal sequence, Cys-X-X-X-X-His-His-X-X-X-X-Lys-X-X-X-Asp-
Val-COOH where each X is individually selected from a group consisting of amino acids, and treating said modified human platelets with said artificial aggregation molecule.

13. The method of claim 12 wherein said synthetic peptide analog has the carboxyl terminal sequence Cys-Tyr-Gly-Gln-Gln-His-His-Leu-Gly-Gly-Ala-
Lys-Gln-AlaGly-Asp-Val-COOH.

14. The method of claim 12 wherein said carrier molecule backbone comprises a protein.

15. The method of claim 12 wherein said carrier molecule backbone comprises human serum albumin.

16. A synthetic molecule capable of replacing fibrinogen in the thrombin or ADP-induced aggregation of human platelets comprising a plurality of synthetic peptide analogs of the platelet receptor recognition site of fibrinogen sulfhydrally grafted to a carrier molecule backbone, each of said peptides having the carboxyl terminal sequence Cys-Tyr-Gly-Gln-Gln
His-His-Leu-Gly-Gly-Ala-Lys-Gln-Ala-Gly-Asp-
Val-COOH.

17. The synthetic molecule of claim 16 wherein said carrier molecule backbone comprises human serum albumin.

* * * * *